United States Patent [19]

Carney et al.

[11] 4,214,077
[45] Jul. 22, 1980

[54] 1-N-SUBSTITUTED DERIVATIVES OF SELDOMYCIN FACTOR 5

[75] Inventors: Ronald E. Carney, Gurnee, Ill.; Stephen Hanessian, Beaconsfield, Canada

[73] Assignee: Abbott Laboratories, North Chicago, Ill.

[21] Appl. No.: 879,415

[22] Filed: Feb. 21, 1978

[51] Int. Cl.$^2$ .............................................. C07H 15/22
[52] U.S. Cl. ................................. 536/17 R; 424/180; 536/4; 536/18; 536/53
[58] Field of Search ......................... 536/17, 4

[56] References Cited

U.S. PATENT DOCUMENTS

| | | | |
|---|---|---|---|
| 3,350,387 | 10/1967 | Vanderhaeghe | 536/17 |
| 3,925,353 | 12/1975 | Umezawa et al. | 536/17 |
| 4,002,608 | 1/1977 | Wright et al. | 536/17 |
| 4,044,123 | 8/1977 | Daniels et al. | 536/17 |

*Primary Examiner*—Johnnie R. Brown

*Attorney, Agent, or Firm*—Robert L. Niblack; Gildo E. Fato

[57] ABSTRACT

Disclosed are compounds of the formula

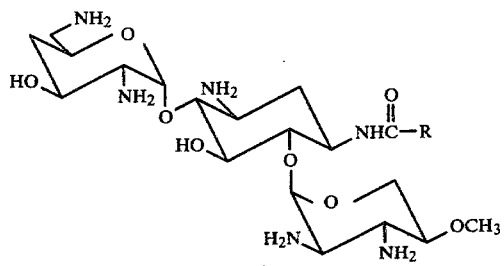

wherein R is loweralkyl, aminoloweralkyl, hydroxyloweralkyl and aminohydroxyloweralkyl and the pharmaceutically acceptable acid addition salts thereof, all of which are potent antibacterials.

10 Claims, No Drawings

1-N-SUBSTITUTED DERIVATIVES OF SELDOMYCIN FACTOR 5

BACKGROUND OF THE INVENTION

Seldomycin Factor 5 is a broad spectrum antibacterial agent elaborated by *Streptomyces hofunensis* and for which the following formula has been elucidated.

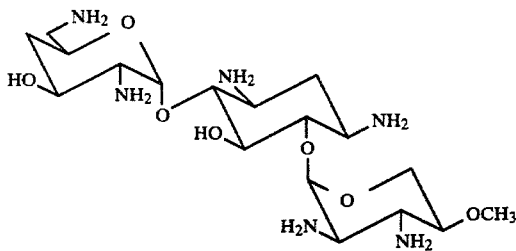

Seldomycin factor 5 is also known as Antibiotic XK-88-5. It is a highly active antibiotic, effective against both Gram-positive and Gram-negative organisms such as *Staphylococcus aureus, Klebsiella pneumoniae, Escherichia coli* and Proteus, Enterobacter and Salmonella species. Seldomycin factor 5 is only one of a number of antibiotics produced by the fermentation of *Streptomyces hofunensis*. The isolation and characteristics of seldomycin factor 5 is described in U.S. Pat. No. 3,939,043 (1976) and the elucidation of its structure is described in the Journal of Antibiotics 30 pages 39–49 (1977).

The nomenclature of the above formula is simplified by the following numbering system in which the carbons of the cylitol moiety, also known as the 2-deoxystreptamine moiety, are numbered 1 through 6. The carbons of the hexose moiety are numbered with a single prime, 1' through 6' and the carbons of the pentose moiety are numbered with a double prime, 1" through 5".

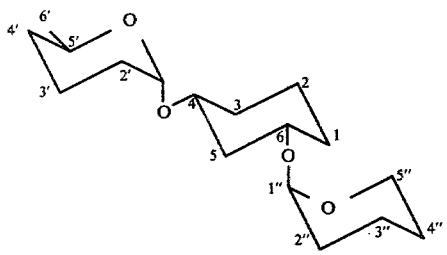

Microorganisms are known to frequently acquire resistance to aminoglycoside antibiotics by a mechanism known in the art as "R-Factors". Very generally an "R-Factor" is the extrachromosomal genetic capability of biochemically modifying the antibiotics in such as way as to interfere with its antibacterial action, thereby enabling the organism to grow.

The difficulty of selectively acylating or alkylating any one amine of an aminoglycoside increases sharply with increasing numbers of amino groups in the molecule. This increase in difficulty is especially marked if the amino groups are all of the same substitution pattern. Thus selective acylation or alkylation at one of the amines of seldomycin factor 5 which contains six primary amines presents a formidable problem.

Other inventions for solutions to this problem have been described. U.S. Pat. No. 4,002,608 describes a method for the preparation of 1-N-alkyl seldomycin factor 5 via initial formation of 2"-N-alkanoyl substituted seldomycin factor 5. No description with respect to the yield from this method nor of the purity of the products are made nor is the method applicable to acylation at the 1-N-position.

SUMMARY OF THE INVENTION

A solution to the noted problem involving novel reaction sequences leading to good yields of pure 1-N-acyl and hence 1-N-alkyl derivatives of seldomycin factor 5 is the subject of this invention. Specifically, a method is described for the preparation of 1-N-acyl derivatives of seldomycin factor 5 via a 3,2',6'-tri-N-protected derivative.

Both the preparation of this intermediate and the subsequent attachment of the 1-N-acyl group can be effected by the method described in good yield and of high purity.

DETAILED DESCRIPTION OF THE INVENTION

In summary, this invention relates to derivatives of seldomycin factor 5, namely 1-N-substituted derivatives which in general exhibit improved activity against a wide range of Gram-positive and Gram-negative bacteria known to be resistant to aminoglycosides. These derivatives are also active against many bacteria not known for their resistance to aminoglycosides. The invention further relates to a method of preparation of these derivatives which proceeds in good yield to give products of high purity. The invention also relates to the intermediates in the preparation of 1-N-substituted derivatives of seldomycin factor 5.

The compounds of the invention are illustrated by the formula

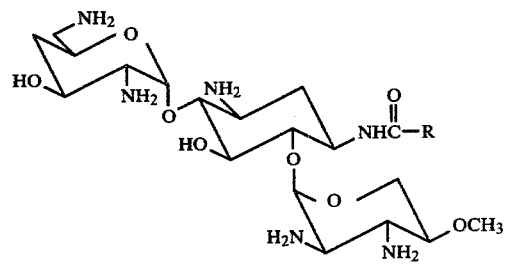

wherein R is selected from the group consisting of loweralkyl, aminoloweralkyl, hydroxyloweralkyl and aminohydroxyloweralkyl and the pharmaceutically acceptable acid addition salts thereof.

In detail, the invention for which a patent is sought involves the following process for the selective acylation of seldomycin factor 5 at the 1-N-position. Seldomycin factor 5 as the free base is dissolved in a polar solvent and allowed to complex with copper sulfate or some other suitable divalent metal salt such as a transition metal ion such as Fe, Co, Ni, Cu, Pd, Ag and Pt. Carbon magnetic resonance studies show that copper (II) ion in dilute solutions complexes most strongly to the 2",3"-diamino system of the pentose ring. Thus reaction of the copper complex of seldomycin factor 5 with an amine-protecting reagent results in the protection of amines other than those of the pentose moiety. Conditions have been found which give good yields of 3,2',6'-tri-N-carbobenzoxyseldomycin factor 5 from treatment of the copper complex of seldomycin factor 5 with an active ester of benzylcarbonic acid. Treatment of a 3,2',6'-tri-N-protected derivative of seldomycin factor 5 with an N-acylating agent in the presence of copper ion lead to good yield of 1-N-acyl-3,2',6'-tri-N-protected derivatives of seldomycin factor 5. These compounds may be deprotected by methods well known in the art to yield 1-N-acyl derivatives of seldomycin factor 5 in high purity. 1-N-Acyl derivatives of seldomycin factor 5 are potent antibacterials with activity against many aminoglycosides sensitive and resistant strains. They are also useful intermediates in the preparation of 1-N-alkyl derivatives of seldomycin factor 5 which are also potent antibacterials.

1-N-Acyl-3,2',6'-protected derivatives of seldomycin factor 5 may also be reduced to 1-N-alkyl-3,2',6'-tri-N-protected derivatives of seldomycin factor 5 and these in turn may be deprotected to yield 1-N-alkyl derivatives of seldomycin factor 5.

In the method described, suitable active esters of carboxylic acids can be used as N-acylating agents. Examples are acid anhydride, acid chloride, or a carboxylic acid ester of N-hydroxy succinimide.

N-protecting reagents are commonly used in the art. Examples of such groups and their removal are described in Kapoor, A., J. Pharm. Sciences, 59, pp. 1–27 (1970) and include carboxylic acid chlorides, bromides or an acid azide. Reference can also be made to U.S. Pat. No. 3,781,268, issued Dec. 25, 1973, for Antibiotic Derivatives of Kanamycin, which describes such reagents and their use.

The following examples are illustrative of the method and compounds of this invention.

EXAMPLE 1

3,2',6'-Tri-N-benzyloxycarbonyl seldomycin factor 5

Seldomycin factor 5 free base (15.0 gm) (33.3 Mmole) was dissolved in methanol (750 ml). Triethylamine (4.66 ml) (1 equivalent) was added, followed by copper sulfate pentahydrate (4.2 gm) (16.7 millimoles) in methanol (50 ml). To a stirred solution of the seldomycin factor 5 copper complex was added the benzyloxycarbonyl ester of N-hydroxy succinimide (30 gm) (120 millimoles). After standing at room temperature overnight the mixture was taken to dryness under reduced pressure. Chromatography of the residue over silica gel using CHCl$_3$—MeOH—NH$_4$OH (50:50:5) as the solvent system gave 9.0 grams of 3,2',6'-tri-N-benzyloxycarbonyl seldomycin factor 5 (30–35% yield).

EXAMPLE 2

1-N-Acetyl-3,2',6'-tri-N-benzyloxycarbonyl seldomycin

To a solution of 3,2',6'-tri-N-benzyloxycarbonyl seldomycin factor 5 (4.0 gm) (4.7 millimoles) in methanol-tetrahydrofuran (3:2) (200 ml) was added copper sulfate pentahydrate (587 mg) (2.3 millimoles) in methanol (40 ml). To a stirred solution of the resulting tri-N-benzyloxycarbonyl seldomycin factor 5 copper complex, acetic anhydride (3.0 ml) was added. The mixture remained at room temperature overnight and was then evaporated to dryness under reduced pressure. Chromatography of the residue over silica gel using CHCl$_3$—MeOH—NH$_4$OH (90:10:1) as the elution solvent afforded 2.2 gm of 1-N-acetyl-3,2',6'-tri-N-benzyloxycarbonyl seldomycin factor 5. (52% yield).

EXAMPLE 3

1-N-(4-Benzyloxycarbamido-2-hydroxybutyryl)-3,2',6'-tri-N-benzyloxycarbonyl Seldomycin Factor 5

A stirred solution of 3,2',6'-tri-N-benzyloxycarbonyl seldomycin factor 5 (512 mg) (0.6 millimole) in methanol-chloroform (3:2) (25 ml) was added to a solution of copper sulfate pentahydrate (50 mg) (0.2 millimole) in methanol (75 ml). to the resulting tri-N-benzyloxycarbonyl seldomycin factor 5 copper complex was added 4-benzyloxycarbamido-2-hydroxybutyric acid ester of N-hydroxysuccinimide (1.0 gm) (2.8 millimole) in portions over a three hour period. The reaction mixture remained at room temperature overnight and the solvent was then removed under reduced pressure. Chromatography of the residue over silica gel using chloroform-methanol-concentrated ammonium hydroxide (90:10:1) as elution solvent afforded 180 mg. of 1-N-(4-benzyloxycarbamido-2-hydroxybutyryl)-3,2',6'-tri-N-benzyloxycarbonyl seldomycin factor 5. (28% yield).

EXAMPLE 4

1-N-(3-Benzyloxycarbamido-2-D,L-hydroxypropionyl)-3,2',6'-tri-N-benzyloxycarbonyl Seldomycin Factor 5

A solution of copper sulfate pentahydrate (69 mg, 0.28 millimole) in methanol (10 ml) was added to a stirred solution of 3,2',6'-tri-N-benzyloxycarbonyl seldomycin factor 5 (924 mg, 1.1 millimole) in methanol:tetrahydrofuran (3:2, v/v, 50 ml). The resulting copper complex was treated with a filtered solution of the N-hydroxy-5-norbornene-2,3-dicarboximide ester of 3-benzyloxycarbamido-2-D,L-hydroxypropionic acid prepared from 3-benzyloxycarbamido-2-D,L-propionic acid (956 mg, 4.8 millimoles), N-hydroxy-5-norbornene-2,3-dicarboximide (876 mg) and dicyclohexyldicarbodiimide (988 mg, 4.8 millimoles) in tetrahydrofuran (50 ml). The reaction mixture was allowed to stand overnight at room temperature and then evaporated to dryness under reduced pressure. Chromatography of the residue over silica gel with chloroform:methanol:ammonium hydroxide (90:10:1, v/v/v) as elution solvent afforded 120 mg of 1-N-(3-benzyloxycarbamide-2-D,L-hydroxypropionyl)-3,2',6'-tri-N-benzyloxycarbonyl seldomycin factor 5.

EXAMPLE 5

1-N-Acetyl Seldomycin Factor 5

1-N-Acetyl-3,2',6'-tri-N-benzyloxycarbonyl seldomycin factor 5 (1.26 gm) (1.4 millimole) was dissolved in methanolic hydrogen chloride (150 ml, 0.2 N) and hydrogenated over 5% Pd-C (1.3 gm) at 3 atmospheres overnight. The catalyst was removed by filtration and the filtrate take to dryness in vacuo to yield 1.2 gm of 1-N-acetyl seldomycin factor 5 pentahydrochloride. Chromatography of the hydrochloride salt over AG1 X2 (OH-) resin afforded 625 mg of 1-N-acetyl seldomycin factor 5 free base.

EXAMPLE 6

1-N-(4-Amino-2-L-hydroxybutyryl)-Seldomycin Factor 5

1-N-(4-Benzyloxycarbamido-2-L-hydroxybutyryl)-3,2',6'-tri-N-benzyloxycarbonyl seldomycin factor 5 (179 mg) (0.164 millimole) was dissolved in methanolic hydrogen chloride (30 ml, 0.2 N) and hydrogenated over 5% Pd-C (200 mg) at 3 atmospheres for six hours. The catalyst was removed by filtration and the filtrate taken to dryness in vacuo to yield 120 mg of 1-N-(4-amino-2-L-hydroxybutyryl) seldomycin factor 5 as its hydrochloride salt. Chromatography of this material over AG1 X2 (OH-) resin afforded 82 mg of 1-N-(4-amino-2-L-hydroxybutyryl) seldomycin factor 5 as the free base.

EXAMPLE 7

1-N-(3-Amino-2-D,L-hydroxypropionyl) Seldomycin Factor 5

1-N-(3-Benzyloxycarbamido-2-D,L-hydroxypropionyl-3,2',6'-tri-N-benzyloxycarbonyl seldomycin factor 5 (120 mg) (0.11 millimole) was dissolved in methanolic hydrogen chloride (30 ml, 0.2 N) and hydrogenated over 5% Pd-C (200 mg) at 3 atmospheres overnight. The catalyst was removed by filtration and the filtrate evaporated to dryness in vacuo to yield 100 mg of 1-N-(3-amino-2-D,L-hydroxypropionyl seldomycin factor 5 as its hydrochloride salt. Chromatography of this material over AG1 X2 (OH-) resin afforded 65 mg of 1-N-(3-amino-2-D,L-hydroxypropionyl) seldomycin factor 5 as the free base.

EXAMPLE 8

1-N-Ethyl-Seldomycin Factor 5

Method I

1-N-Acetyl seldomycin factor 5 pentatrifluoroacetate salt (970 mg, 1 millimole) was dissolved in tetrahydrofuran (75 ml) and treated with diborane in tetrahydrofuran (5 ml, IM). The mixture stirred at room temperature overnight. An additional aliquot of diborane in tetrahydrofuran (7 ml, IM) was added and the mixture refluxed for 2 hours. The excess diborane was consumed by the careful addition of water and the mixture taken to dryness in vacuo. Chromatography of the residue over AG1 X2 (OH-) resin afforded 235 mg of 1-N-ethyl seldomycin factor 5 as its free base in a 75% state of purity. This material was chromatrahed over silica gel in isopropanol, chloroform, concentrated ammonium hydroxide (2:1:1) to give pure 1-N-ethyl seldomycin factor 5.

Method II

1-N-Acetyl-3,2',6'-tri-N-benzyloxycarbonyl seldomycin factor 5 (500 mg) (0.56 millimole) was dissolved in tetrahydrofuran (200 ml) and diborane in tetrahydrofuran (5 ml, IM) was added. After three hours at room temperature excess diborane was consumed by the careful addition of water and the mixture taken to dryness in vacuo. Chromatography of the residue over silica gel in chloroform, methanol, concentrated ammonium hydroxide (75:25:2) afforded 70 mg of 3,2',6'-tri-N-benzyloxycarbonyl-1-N-ethyl seldomycin factor 5. Removal of the benzyloxycarbonyl-N-protecting groups by hydrogenolysis over 5% Pd-C in 43 ml of 0.2 N methanolic HCl at 3 atmospheres and chromatography of the product over AG1 X2 (OH-) resin afforded 35 mg of 1-N-ethyl seldomycin factor 5 as its free base.

These compounds are further characterized by their carbon magnetic resonance spectra some of which are listed according to their probable assignments as follows: Only signals assigned to the sugar and cyclitol carbons are given.

| | Compound of Example 1 | Compound of Example 2 | Compound of Example 3 | Compound of Example 4 |
|---|---|---|---|---|
| C-1' | 99.3 | 99.1 | 99.5 | 99.4 |
| C-2' | 57.5 | 57.0 | 57.4 | 57.4 |
| C-3' | 64.7 | 64.8 | 64.6 | 64.5 |
| C-4' | 36.8 | 37.1 | 37.0 | 37.0 |
| C-5' | 66.7 | 66.8 | 66.7 | 66.7 |
| C-6' | 44.5 | 44.5 | 44.5 | 44.4 |
| C-1 | 50.4 | 50.0 | 50.3 | 50.3 |
| C-2 | 37.0 | 34.2 | 34.2 | 34.3 |
| C-3 | 50.2 | 47.6 | 48.1 | 48.1 |
| C-4 | 82.2 | 82.2 | 82.0 | 82.3 |
| C-5 | 73.8 | 74.9 | 74.6 | 74.8 |
| C-6 | 86.4 | 81.5 | 80.3 | 80.3 |
| C-1'' | 98.5 | 98.1 | 98.3 | 98.6 |
| C-2'' | 55.8 | 54.8 | 55.6 | 55.5 |
| C-3'' | 54.7 | 53.8 | 54.3 | 54.6 |
| C-4'' | 80.3 | 79.3 | 80.3 | 80.3 |
| C-5'' | 59.7 | 59.5 | 59.8 | 59.6 |
| OCH$_3$ | 59.9 | 57.6 | 57.9 | 57.9 |
| C-1' | 102.4 | 102.3 | 102.4 | 102.1 |
| C-2' | 57.7 | 57.7 | 57.7 | 57.6 |
| C-3' | 69.1 | 69.1 | 69.1 | 69.0 |
| C-4' | 36.9 | 37.0 | 36.9 | 36.8 |
| C-5' | 71.4 | 71.4 | 71.4 | 70.7 |
| C-6' | 45.7 | 45.7 | 45.7 | 45.5 |
| C-1 | 49.8 | 50.2 | 49.9 | 57.0 |
| C-2 | 35.3 | 35.2 | 35.4 | 32.8 |
| C-3 | 49.8 | 49.8 | 49.9 | 50.0 |
| C-4 | 87.4 | 87.3 | 87.4 | 87.3 |
| C-5 | 75.5 | 75.6 | 75.6 | 75.0 |
| C-6 | 82.6 | 81.6 | 82.1 | 85.1 |
| C-1'' | 99.8 | 99.5 | 99.9 | 100.2 |
| C-2'' | 55.9 | 55.9 | 55.9 | 56.1 |
| C-3'' | 54.2 | 54.2 | 54.3 | 54.7 |
| C-4'' | 80.3 | 80.2 | 80.2 | 80.2 |
| C-5'' | 60.7 | 60.8 | 60.8 | 61.0 |
| OCH$_3$ | 58.6 | 58.6 | 58.6 | 58.7 |

Spectra were measured in DMSO-d6 with tetramethyl silane as the internal standard (Examples 1, 2, 3 and 4) or in deuterium oxide with dioxane as the internal standard (Examples 5, 6, 7 and 8).

| Organism | Seldomycin Factor 5 | Compound of Example 5 | Compound of Example 6 | Compound of Example 7 | Compound of Example 8 |
|---|---|---|---|---|---|
| *Bacillus subtilis* U. of Ill. 10707 | 0.08 | 10 | 0.04 | 0.63 | 0.63 |
| *Staphylococcus aureus* ATCC-6538P | 0.16 | 10 | 0.63 | 1.25 | 1.25 |
| *Enterobacter cloacae* ST-10 | >20 | >20 | 2.5 | 20 | >20 |
| *Eschericia coli* ATCC-26 | 0.31 | 20 | 0.63 | 1.88 | 0.94 |

-continued

| Organism | Seldomycin Factor 5 | Compound of Example 5 | Compound of Example 6 | Compound of Example 7 | Compound of Example 8 |
|---|---|---|---|---|---|
| E. coli 76-2 | 2.5 | >20 | 0.31 | 2.5 | 0.63 |
| E. coli R-5 | >20 | >20 | 0.63 | 2.5 | 5 |
| E. coli R-12 | 0.31 | 20 | 0.31 | 1.25 | 0.63 |
| E. Coli R-16 | 2.5 | 20 | 0.08 | 0.31 | 0.31 |
| E. coli R-17 | 0.31 | >20 | 0.31 | 10 | 10 |
| E. coli R-18 | 0.63 | 20 | 0.31 | 0.63 | 0.31 |
| E. coli R-19 | 5 | >20 | 0.31 | 0.63 | 1.25 |
| E. coli R-20 | >20 | >20 | 0.31 | 2.5 | 5 |
| E. coli NR-79 | 5 | >20 | 0.63 | 5 | 20 |
| Klebsiella pneumoniae ATCC-8045 | 0.04 | 5 | 0.08 | 0.31 | 0.63 |
| K. pneumoniae Y-58 | >20 | >20 | 0.63 | 1.25 | 1.25 |
| K. pneumoniae KY-4262 | 2.5 | >20 | 0.31 | 2.5 | 2.5 |
| K. pneumoniae K-1296 | >20 | >20 | 0.31 | 1.25 | 2.5 |

What is claimed is:

1. A compound of the formula

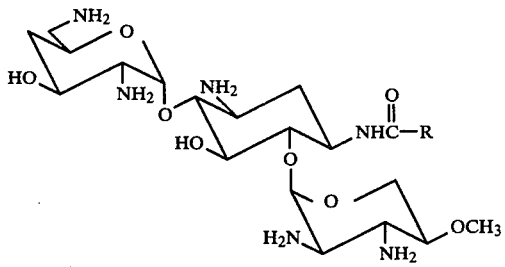

wherein R is selected from the group consisting of loweralkyl, aminoloweralkyl, hydroxyloweralkyl, aminohydroxyloweralkyl with the proviso that R cannot be aminohydroxybutyryl and the pharmaceutically acceptable acid addition salts thereof.

2. The compound of claim 1 wherein R is methyl.

3. The compound of claim 1 wherein R is aminopropyl.

4. A method for the preparation of 1-N-acyl derivatives of seldomycin factor 5 which method comprises reacting an appropriate 3,2',6'-tri-N-protected derivative of seldomycin factor 5 with a transition metal ion to form a metal complex, treating the complex so formed with an N-acylating agent, and subsequently removing the N-protecting groups and dissociating the complex.

5. The method of claim 4 wherein the transition metal ion is selected from the group consisting of Fe, CO, Ni, Cu, Pd, Ag and Pt.

6. The method of claim 5 wherein the transition metal ion is Cu II.

7. A method for the preparation of 1-N-alkyl derivatives of seldomycin factor 5 which method comprises: reducing an appropriate 1-N-acyl-3,2',6'-tri-N-protected derivative of seldomycin factor 5 with a suitable metal hydride reducing agent and removing the N-protected groups.

8. A method for the preparation 3,2',6'-tri-N-protected seldomycin factor 5 which method comprises reacting seldomycin factor 5 with a transition metal ion to form a metal complex, treating the complex so formed with an N-protecting reagent, and subsequently dissociating the metal complex.

9. The method of claim 8 wherein the transition metal ion is selected from the group consisting of Fe, Co, Ni, Cu, Pd, Ag, and Pt.

10. The method of claim 9 wherein the transition metal ion is Cu II.

* * * * *